(12) United States Patent
Bureau et al.

(10) Patent No.: US 9,884,142 B2
(45) Date of Patent: Feb. 6, 2018

(54) DRUG ELUTING STENT WITH A BIODEGRADABLE RELEASE LAYER ATTACHED WITH AN ELECTRO-GRAFTED PRIMER COATING

(71) Applicant: Alchimedics, Grenoble (FR)

(72) Inventors: Christophe Bureau, St. Martin D'Uriage (FR); Ferial Haroun, Grenoble (FR); Elodie Henault, Antony (FR)

(73) Assignee: ALCHIMEDICS, Massy (FR)

( * ) Notice: Subject to any disclaimer, the term of this patent is extended or adjusted under 35 U.S.C. 154(b) by 287 days.

(21) Appl. No.: 13/850,679

(22) Filed: Mar. 26, 2013

(65) Prior Publication Data
US 2014/0296967 A1    Oct. 2, 2014

Related U.S. Application Data

(63) Continuation of application No. 11/808,926, filed on Jun. 13, 2007, now abandoned.
(Continued)

(51) Int. Cl.
*A61L 31/10*    (2006.01)
*A61L 31/14*    (2006.01)
(Continued)

(52) U.S. Cl.
CPC ........... *A61L 31/148* (2013.01); *A61L 31/022* (2013.01); *A61L 31/10* (2013.01); *A61L 31/16* (2013.01);
(Continued)

(58) Field of Classification Search
CPC .. A61F 2002/30003; A61F 2002/30006; A61F 2002/30062; A61F 2002/30064; A61F 2210/0076; A61F 2250/0067; A61L 31/10; A61L 31/16; A61L 2300/416; A61L 2420/02; A61L 2420/04; A61L 2420/06;
(Continued)

(56) References Cited

U.S. PATENT DOCUMENTS 6,120,904 A *    9/2000  Hostettler .............. A61L 29/085
                                                       428/423.3
8,563,041 B2 *  10/2013  Grayson .............. A61K 9/0019
                                                       424/489
(Continued)

FOREIGN PATENT DOCUMENTS

FR    2843757 A1 *    2/2004  ........... C09D 5/4476

OTHER PUBLICATIONS

Bhattacharya A. et al., "Grafing: a versatile means to modify polymers techniques, factors and applications." Prog. Polym. Sci., 29:767-814 (2004).
(Continued)

*Primary Examiner* — Thomas J Sweet
*Assistant Examiner* — Seema Mathew
(74) *Attorney, Agent, or Firm* — Finnegan, Henderson, Farabow, Garrett & Dunner, L.L.P.

(57) ABSTRACT

The present invention provides a drug eluting stent including a metallic stent framework, an electro-grafted primer coating disposed on the stent framework; and a biodegradable polymer coating hosting a drug disposed on the electro-grafted primer coating and a method of manufacturing said biodegradable drug eluting stent.

18 Claims, 3 Drawing Sheets

Drug eluting stent

Biodegradable coating hosting a drug

Electro-grafted coating

Stent framework

Related U.S. Application Data

(60) Provisional application No. 60/812,990, filed on Jun. 13, 2006.

(51) Int. Cl.
 *A61L 31/16* (2006.01)
 *A61L 31/02* (2006.01)

(52) U.S. Cl.
 CPC ..... *A61L 2300/416* (2013.01); *A61L 2420/02* (2013.01); *A61L 2420/06* (2013.01)

(58) Field of Classification Search
 CPC .... A61L 2420/08; A61L 27/54; A61L 31/148; A61L 2300/606; A61L 2300/608; A61L 2400/18; A61L 27/58
 See application file for complete search history.

(56) References Cited

U.S. PATENT DOCUMENTS

| | | | |
|---|---|---|---|
| 9,056,153 B2 * | 6/2015 | Chen | A61L 27/16 |
| 2002/0018795 A1 * | 2/2002 | Whitbourne | A61K 9/0024 |
| | | | 424/414 |
| 2002/0051730 A1 * | 5/2002 | Bodnar | A61L 31/10 |
| | | | 422/33 |
| 2002/0065551 A1 * | 5/2002 | Koole | A61L 31/10 |
| | | | 623/1.25 |
| 2004/0053381 A1 | 3/2004 | Williams et al. | |
| 2004/0144655 A1 | 7/2004 | Bertrand et al. | |
| 2005/0125054 A1 | 6/2005 | Bhat et al. | |
| 2005/0267565 A1 * | 12/2005 | Dave et al. | 623/1.15 |
| 2006/0013853 A1 | 1/2006 | Richard | |
| 2006/0184226 A1 | 8/2006 | Austin | |
| 2007/0209943 A1 * | 9/2007 | Bureau | C09D 5/24 |
| | | | 205/317 |
| 2010/0081992 A1 * | 4/2010 | Ehrenreich | A61L 29/16 |
| | | | 604/103.02 |
| 2015/0174298 A1 * | 6/2015 | Brouzes | A61L 27/34 |
| | | | 424/409 |
| 2016/0177109 A1 * | 6/2016 | Hendricks | D06M 15/3566 |
| | | | 428/36.91 |

OTHER PUBLICATIONS

Geoghegan M., "Linear polymers in networks: swelling, diffusion, and interdigitation," Adv. in Solid State Phys., 45:29-44 (2005).

Maeda N. et al., "Adhesion and friction mechanisms of polymer-on-polymer surfaces," Science, 297:379-82 (2002).

Wikipedia entry for "adhesion" downloaded Jul. 3, 2011.

* cited by examiner

Drug eluting stent

Biodegradable coating hosting a drug

Electro-grafted coating

Stent framework

Figure 3

DRUG ELUTING STENT WITH A BIODEGRADABLE RELEASE LAYER ATTACHED WITH AN ELECTRO-GRAFTED PRIMER COATING

This is a continuation of application Ser. No. 11/808,926, filed Jun. 13, 2007, now abandoned, which is a non-provisional application of provisional Application No. 60/812,990, filed Jun. 13, 2006.

FIELD OF THE INVENTION

This invention relates to drug eluting stents. More specifically, the invention relates to an adhesion primer to be applied to the surface of a metallic stent that may be subsequently coated with a biodegradable polymer itself capable of hosting a drug and releasing it in a sustained manner.

BACKGROUND OF THE INVENTION

Over the years, the use of coatings for medical devices and drug delivery has become a necessity, notably for augmenting the capabilities of medical devices and implants. Drug eluting medical device coatings have emerged as a leading biomedical device for the treatment of cardiovascular disease.

Heart disease and heart failure are two of the most prevalent health conditions in the US and the World. In coronary artery disease, the blood vessels on the heart become narrow. When this happens, the oxygen supply is reduced to the heart muscle. The primary cause of coronary artery disease is fat deposits blocking the arteries ("plaque"). The treatment of coronary artery disease has been initially done by surgery and CABG (Coronary Artery Bypass Graft), which are normal and efficient procedures done by cardiac surgeon. The mortality and morbidity, however, were high. In the 60's, some physicians developed a low invasive treatment by using medical devices. By going through a small incision at the femoral artery, they were able to treat the disease: balloon angioplasty (used to widen an artery that has become narrowed using a balloon catheter which is inflated to open the artery. PTCA=Percutaneous Transluminal Coronary Angioplasty) is used in patients with coronary artery disease. Following balloon angioplasty, approximately 40 to 50% of coronaries arteries are affected by restenosis (the re-narrowing of a blood vessel after it has been opened, usually by balloon angioplasty) within 3 to 6 months due to either thrombosis (the development of a blood clot in the vessels which may clog a blood vessel and stop the flow of blood) or abnormal tissue growth. As a result, restenosis constitutes the major limitation to the effectiveness of the PTCA.

The introduction of the Bare Metal Stent (BMS), in the late 80's, used to keep coronary arteries expanded, went some way towards alleviating this problem, as well as that of the dissections of arteries upon balloon inflation in the PTCA procedure. The stent is mesh tube mounted on a balloon catheter (a long thin flexible tube that can be inserted into the body; in this case, it is threaded to the heart). But the BMS continues to be associated with a restenosis rate of around 25% of patients affected 6 months after stent insertion: stent struts end up embedded by the arterial tissue in growth. This tissue is essentially made of smooth muscle cells (SMC's), the proliferation of which is provoked by the initial damaging of the artery upon stent apposition. The apposition indeed destroys the layer of endothelial cells (EC's) which have to further proliferate and migrate in order to recolonize the stent struts over the SMC's in order to stop their proliferation.

The Biomed industry partly solved this failure rate by designing a new generation of stents providing a coating able to release selected drugs (Sirolimus, Paclitaxel, ABT578, Tacrolimus, Everolimus . . . ) in the vessel walls, in order to prevent restenosis. The Drug Eluting Stent (DES) attracted increasing attention during the late 90's as potentially offering a more effective way to lower the rate of restenosis to a single figure. Ideally, the drug should prevent the proliferation of the SMC's while allowing early recolonization by active EC's, as the latter cells spontaneously produce nitrogen oxide (NO), a small molecule acting as a signal to stop the proliferation of SMC's.

Most DES on the market are made on the basis of a polymeric release matrix from which the drug is eluted. The polymer is so called biostable: the polymer stays permanently on the stent, and is thus assumed to have little effect both on the inflammatory response and the recolonization by EC's. The main drawback of these DES is that they cannot release 100% of the drug they host. One significant consequence of this is that the recolonization process is hindered by the drug remaining in the coating (as most of the drugs "kill" EC's equally or more efficiently than SMC's). This drawback has potentially lethal and dramatic consequences for the patients and thus, for the DES industry. Indeed, despite the fact that restenosis could be lowered down from ca. 20% with BMS to ca. 5% with DES, the industry is presently facing a major challenge revealed and unsolved by the current DES: the phenomenon of late thrombosis, i.e. re-clotting of the artery one year or more after stent implantation.

It has long been known that the implantation of bare metal stents was also the source of thrombosis, in addition to restenosis, but that the former could be easily coped with by a systemic bi-therapy associating two anti-thrombotic agents, typically aspirin and clopidogrel (Plavix®). Typically, patients to whom a stent was opposed were thus prescribed such a bi-therapy for 1 to 2 months. Follow-up data have long pointed out the excellent results of this combination as regards thrombosis. With drug eluting stents, numerous cases of re-clotting of the artery due to coagulation (thrombosis) soon after the interruption of the bi-therapy have been reported, which pushed cardiologists to maintain the bi-therapy for 3, 6, 9 and now 12 months or more. Several cases were reported that myocardial infarction with total stent thrombosis may occur only a couple of weeks after interruption of a 18 month bi-therapy.

Late thrombosis is an abrupt complication which can be lethal when occurring if the patient is not under medical follow-up or—even if he is—while the patient is away from the cathlab or from an adequately equipped medical centre. Moreover, bi-therapy is a very uncomfortable bottleneck, as some patients either decide by themselves to stop it after a period they estimate as long, or may forget to have their medicines, or may have to undergo a clinical intervention which could not be anticipated, and are thus in the position to have to stop the anti-thrombotic treatment.

The exact reasons accounting for the phenomenon of late thrombosis are still incompletely understood. Pathologists estimate that the late thrombosis issue reveals an incomplete recolonization of the stent by EC's, leaving metallic or polymeric materials in contact with the blood over prolonged periods, on which platelet adhesion is likely to occur and lead to catastrophic precipitation of a thrombus. Alternate interpretations have emerged which claim that the incomplete recolonization by EC's is the result of the incomplete release of the drug from the release layer, which "kills" migrating EC's in their attempt to migrate and proliferate on the surface of said polymer+drug layer.

Thus, risks of late thrombosis are a severe drawback of existing DES.

Due to the very high mechanical constraints a stent is facing during its manufacturing process (crimping on the balloon), during its travel in the artery (especially over calcified lesions) and during its expansion (the diameter of the stent is increased by a factor of 3 to 5), uncontrolled crackings and delaminations are often the rule. Crackings and delaminations may provoke an artificial "roughness" which ranges from a few tens of microns to several millimeters, and which is thus prone to seriously hinder the proper recolonization of the stent by EC's.

However "roughness" alone cannot account alone for hinders of recolonization by EC's. A study evaluating the recolonization by EC's obtained at 28 days in pig arteries with two overlapping Cypher® or two Taxus® stents in the same artery, as compared to their respective bare metal counterparts, i.e. two Bx Velocity® or two Express® in the same artery, respectively, evidence that:

even though the "roughness" of the surface to be recolonized is fairly high with both the DES and the BMS (because of the overlap between the two stents), the recolonization is always better with the BMS as compared to the DES;

whatever the DES, Cypher® or Taxus®, i.e. whatever the drug which is being released, the recolonization is always better with the corresponding BMS.

This result strongly suggests that, aside of the "roughness" of the coating and of the stent surface after deployment, recolonization is always superior in the absence of drug. This is to be correlated with the fact that:

all existing DES have a biostable layer. The release of the drug is obtained by pure diffusion, and thus can never be complete: there is always some drug left in the coating to be recolonized over prolonged periods;

all drugs in use in existing DES (Sirolimus, Paclitaxel) have a threshold toxic concentration which is comparable or even lower against EC's as compared to SMC's, i.e. they can "kill" EC's equally well or even better than SMC's.

This points to a severe drawback of existing DES in that they locally maintain drugs which are toxic to the EC's over prolonged periods.

Last but not least, these drugs may have an effect on the remodelling of the artery. It was noted a so called "stent malaposition" showing that some of the stet struts were incompletely in contact with the walls of the arteries. It is believed that most stent malapositions are due to the effect of the drug, especially in the case of Sirolimus, which provokes a so called "positive remodelling" of the artery, i.e. its progressive overdilatation: the stent is initially well in contact with the artery walls, but eventually "floats" within the artery which diameter increases under the effect of the drug. In such a case, some of the stent struts remain non recolonized by EC's (as they are too far away from the artery wall) and can be the source of a thrombosis stemming from the direct contact of the polymer material with the blood. Such a thrombosis may not appear as long as the patient is under anti-platelet bi-therapy, but soon starts right after the bi-therapy is interrupted (late thrombosis). This, again, points to the severe drawback of existing drug eluting stents due to the prolonged stay of the drug on the surface of the stent.

OBJECT OF THE INVENTION

The aim of the invention is to provide a stent behaving like a DES in the short term in order to prevent restenosis, and having a long term history resembling that of a BMS in order to avoid thrombosis and allow for early proliferation and migration of EC's prior to remodelling. As detailed previously, late thrombosis is thought to be related to:

incomplete release of the drug;

poor coating integrity due to lack of adhesion of the coating onto the stent surface, leading to crackings and delaminations which are potential sources of "roughness" hindering the recolonization by EC's;

poor pro-healing (long term) behaviour of the coating for EC recolonization in cases of incomplete stent apposition (ISA) due to the drug.

In the DES according to the invention the drug, if any, is released via a biodegradable polymer, which will have disappeared after few weeks, hence releasing 100% of the drug. The manufacturing of coatings making use of such biodegradable polymers must proceed via the use of an adhesion underlayer in order to notably promote good mechanical integrity for proper stent apposition.

Accordingly, it is proposed a drug eluting stent, comprising:

a stent framework;

a electro-grafted coating disposed on the stent framework, and a biodegradable polymer coating hosting a drug disposed on the electro-grafted coating.

The DES may further comprise a biodegradable topcoat layer.

The electro-grafted coating is used as an effective primer coating to promote adhesion between the metal stent surface and the subsequent polymer coating. The electro-grafted coating may be applied to the stent and dried, followed by the drug polymer being applied. The subsequent polymer coating may contain one or more therapeutic compounds to provide pharmaceutical properties to the drug eluting stent. The primer electro-grafted coating acts as a bridge between substrates and organic polymer coatings, with good adhesion properties to the metal and to the drug polymer.

Electro-grafting technology allows covalent bonding onto the surface, giving layers of a few tens of nanometers to a few hundreds of nanometers, and nanometric control as well as the deposition of materials which are known to the vascular such as p-BuMA. Furthermore the obtained electro-grafted layers are uniform and conformal to the stent surface. Said electro-grafted coating (i) either disappears itself, i.e. is itself biodegradable; or (ii) shows good propensity for cell migration and proliferation, and in particular is absolutely uniform and free of cracking and delamination. As the biodegradable release matrix disappears, this underlayer will be in contact either with EC's or SMC's (recolonization underway) or with the blood (incomplete recolonization, ISA . . . etc), or both. It is thus of primary importance that said underlayer be itself as much uniform as possible, and in particular that it did not crack, which would be a hinder to the full recolonization by EC's.

BRIEF DESCRIPTION OF THE FIGURES

FIG. 3 shows a drug eluting stent comprising a biodegradable coating hosting a drug, an electro-grafted coating, and a stent framework.

DETAILED DESCRIPTION OF THE PRESENTLY PREFERRED EMBODIMENTS

Figure 1A:
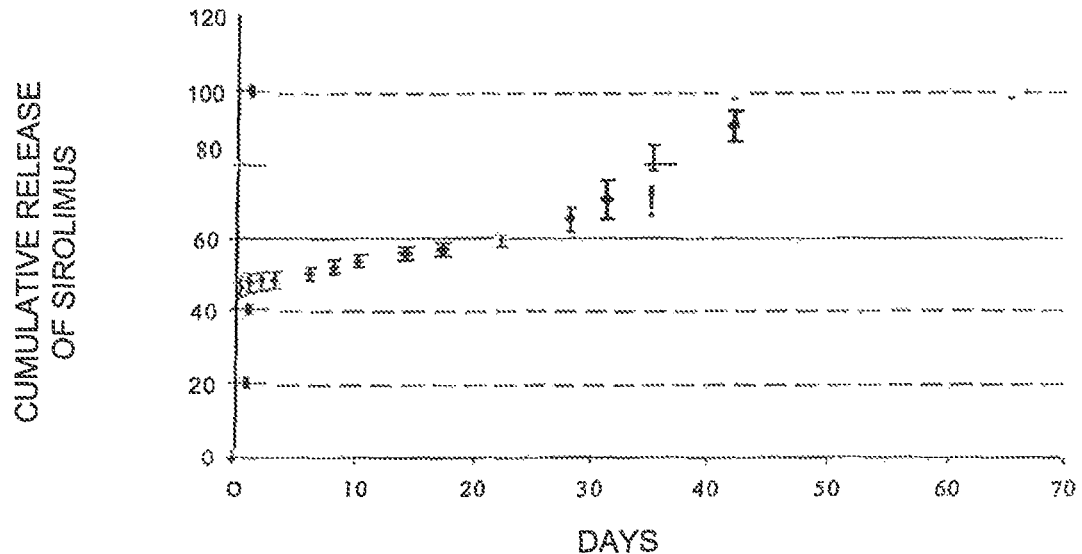
FIG. 1(A) shows the cumulative release of Sirolimus over the time (days) from a double layer coating of PLGA, in vitro.

A first object of the invention is a drug eluting stent (DES), comprising:
- a stent framework;
- a electro-grafted coating disposed on the stent framework, and
- a biodegradable polymer coating hosting a drug disposed on the electro-grafted coating The Stent Framework The stent framework advantageously comprises a metallic base. In particular, the stent framework comprises a material selected from the group consisting of stainless steel, nitinol, tantalum, cobalt-chromium MP35N or MP20N alloys, platinum, titanium, a suitable biocompatible alloy, a suitable biocompatible material, and a combination thereof.

The Electro-Grafted Coating

The electro-grafted layer works as an adhesion primer for the upper biodegradable layer (during manufacturing, crimping and stenting procedure). The electro-grafted primer coating is a uniform layer. This layer has preferably a thickness between 10 nm and 1.0 micron, in particular a thickness between 10 nm and 0.5 micron, more particular between 100 nm and 300 nm. Such a thickness, which is lower than the minimum radius of curvature reachable at any point of the stent surface, may ensure that the coating does not crack. Electro-grafted layers are capable of preventing the cracking and delamination of biodegradable polymer layers, and show equal if not better recolonization than stainless steel BMS. Furthermore, the use of an electro-grafted layer having a thickness at least about a few tens or of a hundred nanometers secures a good reinforcement of adhesion of the upper biodegradable layer, thanks to interdigitation between the two polymeric layers. In that sense, the choice of the nature of the electro-grafted polymer is based upon the nature of the release matrix polymer, which itself is chosen on the basis of the loading and kinetics of drug release which are desired: the electro-grafted polymer and the release matrix polymers have to be partially miscible to constitute a good interface. This is the case when e.g. the two polymers have close solubility or Hildebrand parameters, or when a solvent of one of the polymers is at least a good swellant to the other. Apart from this constraint, the nature of the electro-grafted polymer is preferably chosen from lists of polymers known to be biocompatible. Last, not all polymers can be obtained via electro-grafting, but most polymers obtained via propagation chain reaction are eligible, such as vinylics, epoxides, cyclic monomers undergoing ring opening polymerization. Thus, poly-Butyl MethAcrylate (p-BuMA), poly-Methyl MethAcrylate (PMMA) or poly-EpsilonCaproLactone (p-ECL) are interesting polymers, obtainable via electro-grafting, to interact with a hydrophobic release matrix. Poly-HydroxyEthyl MethAcrylate (p-HEMA) is an interesting polymer, obtainable via electro-grafting, to interact with a hydrophilic release matrix.

Other organic film, obtainable by electro-grafting but which are not of "real" polymeric nature, can be very efficient primer layers for release matrix: this is the case for "poly"-nitro-phenyl films obtained thanks to the electro-grafting of phenyl diazonium salts, in particular 4-aminophenyl diazonium tetrafluoro borate, on the stent surface prior to spray of the release matrix. The phenyl diazonium salt is preferably of formula $Y-ArN_2^+X^-$, in which Ar represents an aryl group, advantageously a phenyl group, X represents an anion advantageously selected among: halogens, sulphates, phosphates, perchlorates, tetrafluoroborates, hexafluorophosphates and carboxylates, and Y is a functional group, advantageously selected among: nitro, hydroxyl, thiol, amino, carboxyl, carbonyl, ester, amido, cyano, alkyl or functionalized alkyl, phenyl or functionalized phenyl.

The electro-grafted layer, in particular a p-BuMA layer, may further have a passivating behaviour and blocks the release of heavy metal ions (in the blood flow or in the artery walls) from the stainless steel surface. Said heavy metal ions are thought to contribute to the initial inflammation caused by the introduction of the metal stent in the blood, which is an electrolytic medium and hence provokes the partial oxidization of any metal until Nernst equilibrium is reached. In particular, it is observed—on longitudinal cross sections—that the thickness of the artery walls of the electro-grafted layer and biodegradable (with no drug) branch of the study are always smaller than those of the bare metal stent branch, evidencing less granuloma i.e. less inflammation: this result is the confirmation of what was observed with the 28 day rabbit study, in which less inflammation was detected with the stents coated with a mere electro-grafted p-BuMA layer as compared to the BMS (see EXAMPLES 11 and 12).

In an embodiment of the invention, the electro-grafted layer is biodegradable itself, and thus disappears from the surface of the stent after the biodegradable release layer has also disappeared.

The electro-grafted layer has a non thrombotic (or thromboresistant) effect and a pro-healing effect (once the biodegradable release layer has gone, promotion of the proliferation and adhesion of active EC's). Should the EC's start proliferating on the top of the drug containing biodegradable layer, i.e. before it has fully disappeared, the mechanism of hydrolysis of the said biodegradable polymers will nevertheless continue underneath, and soon the EC's will be in contact with the electro-grafted layer. The pro-healing effect is expected to be that of the stainless steel surface if the electro-grafted layer is biodegradable itself. The pro-healing effect is greater with a biostable electro-grafted layer which secures proper recolonization by EC's in the longer term.

A 60 day pig trial has been conducted and described in EXAMPLE 13 with a composite layer made of an electro-grafted p-BuMA (poly-Butyl methacrylate) underlayer (150 nm) overcoated with a PLGA (poly-lactide-co-glycolide) biodegradable release layer (5 μm). This study could first show that the biodegradable release layer had disappeared after the first 4 weeks, hence releasing 100% of the drug. It also demonstrated that stents coated with electro-grafted layer and biodegradable layers are fully recolonized by endothelial cells at 8 weeks: since the biodegradable layer is known to have disappeared after 4 weeks, this means that the good recolonization is the result of the interaction of the electro-grafted layer alone with the artery and blood flow.

The overall performance of electro-grafted layer and biodegradable stents is statistically superior to BMS, even in the (difficult) situation of a composite bi-layer (electro-grafted layer+biodegradable reservoir) in which there is no drug inside the biodegradable release layer. DES according to the invention would enable the interruption of anti-platelet bi-therapy soon after the implantation of the stent thanks to a better recolonization by EC's.

Thrombosis being a phenomenon starting via the adhesion of specific proteins on the surface, a thromboresistant behaviour is to be related to the propensity of the surface to minimize or even eliminate protein adsorption. Several types of macromolecules are known to have this anti-fouling effect such as heparin, CMDBS, PC (phosphoryl-choline) based polymers and more generally macromolecules bearing zwitterionic groups, poly-ethylene oxide (PEO) or poly-ethylene glycol (PEG) and more generally almost any highly hydrophobic surface. What these polymers have in common is that they bear very little—if any—reactive function prone to facilitate the bonding of proteins at their surface.

In short, the electro-grafted layer could additionally be made of such anti-fouling materials, as long as they are also compatible with the aforementioned criteria enabling a good interface with the release matrix polymer, in order to have acceptable thromboresistant behaviour. This requirement is not contradictory to the property the electro-grafted layer has to fulfil as a primer layer which is to improve the adhesion of the thick biodegradable layer to the metallic surface of the stent, since—as we have seen above—the adhesion to the release matrix polymer is mainly stemming from interdigitation with the electro-grafted polymer. One shall note that the PC polymer developed by Biocompatibles Plc. is a vinylic polymer, and can thus be obtained by electro-grafting (p-MPC/BUMA, p-MPC/DMA/TMSPMA, see below).

Among the polymers which can be used as electro-grafted coating mention may in particular be made of vinyl polymers, such as, for example, polymers of acrylonitrile, of methacrylonitrile, of methyl methacrylate, of ethyl methacrylate, of propyl methacrylate, of butyl methacrylate, of hydroxyethylmethacrylate, of hydroxylpropylmethacrylate, of cyanoacrylates, of acrylic acid, of methacrylic acid, of styrene and of its derivatives, of N-vinylpyrrolidone, of vinyl halides, and polyacrylamides; polymers of isoprene, of ethylene, of propylene, of ethylene oxide, of molecules containing a cleavable ring, such as lactones, and in particular ε-caprolactone, of lactides, of glycolic acid, of ethylene glycol, polyamides, polyurethanes, poly(orthoesters) and polyaspartates.

The organic film obtained by electro-grafting can be a vinylic polymer or copolymer, in particular poly-BUMA (poly butyl methacrylate), poly-HEMA (poly hydroxyethylmethacrylate), poly-MPC/BUMA (poly 2-methacryloyloxyethyl phosphorylcholine/butyl methacrylate) and poly-MPC/DMA/TMSPMA (poly-methacryloyloxyethyl phosphorylcholine/dodecyl methacrylate/trimethylsilylpropylmethacrylate). In an embodiment, the organic film is a biodegradable polymer, in particular a polycaprolactone, a polylactide (PLA) or a polyglycolactide (PLGA).

Adhesion Between the Electro-Grafted Coating and the Biodegradable Layer (Drug Containing Layer or Topcoat Layer)

The upper biodegradable layer may adhere onto the electro-grafted layer by:
  forming a chemical bond with the electro-grafted polymer (see for example patent application WO04/005410, herein enclosed by reference);
  inserting in the electro-grafted polymer chemical precursors of the said biodegradable layer, in order to provoke its formation inside the electro-grafted polymer film, which will then act as an anchoring layer for the said biodegradable layer (see for example patent applications WO04/074537 and WO04/075248, herein enclosed by reference);
  forcing the interpenetration of pre-formed biodegradable polymer inside the electro-grafted layer by interdigitation. Interdigitation is related to the fact that the polymeric chains of the said biodegradable polymer can "creep" or "reptate" inside the electro-grafted layer, and make at least one "loop" inside the electro-grafted layer. For a polymer, one "loop" is the typical size of a chain when at random configuration: it can be evaluated by the measure of the so called radius of gyration of the polymer. Even though it is somewhat related to the precise polymer, to its molecular structure . . . etc, the radius of gyration of a polymer is most of the time smaller than 100 nm, suggesting that to enable improved adhesion, electro-grafted layers have to be thicker than this threshold value to be capable of hosting at least one loop of the polymer the upper layer is made of.

Interdigitation is a way to obtain excellent adhesion of the biodegradable layer onto the electro-grafted layer, provided the latter:
  is thicker than about 100 nm;
  has a wettability (i.e. hydrophobic/hydrophilic) identical to that of the upper biodegradable polymer to enable "mixing" in between the two;
  has a glass transition temperature smaller than that of the upper biodegradable polymer in order to obtain thermal interdigitation at low enough a temperature preserving the drug stability; or
  is at least swollen by a solvent of the said upper biodegradable polymer or a solvent containing a dispersion of the said upper biodegradable polymer or of its components, so that interdigitation can be forced efficiently by the apposition of a mere droplet of such liquid on the surface of the electro-grafted layer, at room temperature: the liquid, which swells the electro-grafted layer, provokes the insertion of the components of the solution or dispersion into the electro-grafted layer, and then evaporates to leave an interdigitated composite material.

This latter condition is sufficient to obtain the formation of a good and strong interface between the biodegradable release layer and the electro-grafted layer.

Interdigitation is a preferred mode of the invention to build the interface between the release matrix and the electro-grafted layer as compared to chemical bonding or layering: since the release matrix is chosen here to be biodegradable, what is left behind is an (electro-grafted) polymer of known structure, i.e. with no unreacted chemical group or hydrolyzed bond that would promote a residual reactivity of the electro-grafted film prone to provoke inflammatory and/or thrombotic reactions.

Interdigitation requires that one can spread a solution containing the biodegradable polymer layer and optionally the drug over a stent coated with an electro-grafted layer, properly chosen to have the desired wettability properties. PLGA, for example, is easily soluble in dichloroethane, dichloromethane or in chloroform, as are most of the hydrophobic drugs such as Sirolimus, Paclitaxel or ABT-578. In such a case, electro-grafted p-BuMA is a proper choice to have the desired interdigitated interface, as it is readily swollen by (and even soluble in) chloroform or dichloromethane.

From the manufacturing standpoint, this spreading can be done either by dipping or by spraying. Dipping is less employed, as it does not enable one to have layers thicker than about 2 to 3 μm per shot: for higher thicknesses, one has to fully dry a first layer before re-dipping, in order to avoid re-dissolution of the layer already deposited. This constraint makes dipping very little convenient for layers above 2 μm. Spraying is easier to implement in this respect (see EXAMPLE 14). A nozzle spraying the above solution is facing the stent, which rotates in order to present all outside surfaces to the spray. In order to be in the above conditions to obtain the proper interdigitated interface, one will advantageously work in so called "wet spray" or "low pressure" conditions: the solution to be sprayed has a low viscosity (typically <1 cP, the viscosity of pure chloroform being 0.58 cP), the nozzle is at short distance from the rotating stent, and the pressure of the inert vector gas (nitrogen, argon, compressed air . . . ) in the nozzle is typically less than 1 bar. These conditions lead to the nebulization of the liquid into small droplets of liquid, which travel in the spraying chamber atmosphere to hit the surface of the electro-grafted stent: since the electro-grafted polymer layer and the spray solution have the same wettability, the droplet shows very low contact angle (=good wetting), and the collection of droplets on the surface are thus filmogenic early on. In addition to preparing a good interface between the biodegradable layer and the electro-grafted layer, "the low pressure" spray system enables the manufacturing of coated stents with very little webbing in between the struts.

The relative movement of the nozzle with respect to the stent enables the deposition of a uniform and relatively thin (<1 μm) layer in a single shot, which is still full of solvent. The rotation and air renewal enable the evaporation of the said solvent, all the more easily as the layer is thin, leaving the polymer layer (+drug) on the surface. A second layer can then be sprayed on the first one and so on, in order to reach the desired thickness (and thus loading). As it imposes several sprays to reach the desired thickness, the "low pressure" spray system may be implemented in batches, in which several stents are rotating in parallel with one nozzle spraying over each and every stent sequentially, enabling the other stents to evaporate dry while another one is being sprayed. This maintains the throughput of the system high enough even though the low pressure spray approach is very sequential in nature.

Such a low pressure spray system is outlined in EXAMPLE 14, which can handle 20 rotating stents per batch and a single nozzle which moves above the stents thanks to a X-Y scanning system. One peculiarity of this system is that the rotating stents are inside the box (to enable solvent extraction and safety of the operator) while the X-Y system is outside the box: the movement of the nozzle is piloted through the ceiling of the box via magnets, preserving the "closed shell" structure of the box to which the sampleholder is plugged to the lateral gate via the removable sample-carrier, and inserted and connected to the rotor in the box upon opening the gate from the inside with the glove.

The Drug Containing Biodegradable Layer

The biodegradable release layer will advantageously have a 1 to 200 μm thickness, more advantageously a ca. 1 to 10 μm thickness, (depending on loading) in order to achieve drug release over a prescribed period.

Drug-polymer coating may include one or more drugs. Each drug may include a bioactive agent. The bioactive agent may be a pharmacologically active drug or bioactive compound. The drug-polymer coating may be subject to degradation during processing, packaging, sterilization, or storage of a drug-polymer eluting stent. During sterilization, for example, oxidation of the drug or polymer may occur, resulting in hydrolytic damage, cleavage of the polymeric bonds, breakdown of the polymer and/or drug, or actual cracking or peeling of the drug-polymer coating. Temperature excursions of the in-process or processed stent may incite delamination of all or a portion of the drug-polymer coating. The present invention solves this problem through the use of an electro-grafted primer coating between the polymer-drug coating and the metallic stent, so as to reduce or prevent drug-polymer delamination.

The drugs may be encapsulated in a drug-polymer coating using a microbead, microparticle or nanoencapsulation technology with albumin, liposome, ferritin or other biodegradable proteins and phospholipids, prior to application on the primer-coated stent.

The bioactive agent may include an antineoplastic agent such as triethylene thiophosphoramide, an antiproliferative agent, an antisense agent, an antiplatelet agent, an antithrombogenic agent, an anticoagulant, an antibiotic, an anti-inflammatory agent, a gene therapy agent, an organic drug, a pharmaceutical compound, a recombinant DNA product, a recombinant RNA product, a collagen, a collagenic derivative, a protein, a protein analog, a saccharide, a saccharide derivative, or combinations thereof.

The bioactive agent may be any therapeutic substance that provides a therapeutic characteristic for the prevention and treatment of disease or disorders. An antineoplastic agent may prevent, kill, or block the growth and spread of cancer cells in the vicinity of the stent. An antiproliferative agent may prevent or stop cells from growing. An antisense agent may work at the genetic level to interrupt the process by which disease-causing proteins are produced. An antiplatelet agent may act on blood platelets, inhibiting their function in blood coagulation. An antithrombogenic agent may actively retard blood clot formation. An anticoagulant may delay or prevent blood coagulation with anticoagulant therapy, using compounds such as heparin and coumarins. An antibiotic may kill or inhibit the growth of microorganisms and may be used to combat disease and infection. An anti-inflammatory agent may be used to counteract or reduce inflammation in the vicinity of the stent. A gene therapy agent may be capable of changing the expression of a person's genes to treat, cure or ultimately prevent disease. An organic drug may be any small-molecule therapeutic material. A pharmaceutical compound may be any compound that provides a therapeutic effect. A recombinant DNA product or a recombinant RNA product may include altered DNA or RNA genetic material. Bioactive agents of pharmaceutical value may also include collagen and other proteins, saccharides, and their derivatives. For example, the bioactive agent may be selected to inhibit vascular restenosis, a condition corresponding to a narrowing or constriction of the diameter of the bodily lumen where the stent is placed. The bioactive agent may generally control cellular proliferation. The control of cell proliferation may include enhancing or inhibiting the growth of targeted cells or cell types.

The bioactive agent may be an agent against one or more conditions including coronary restenosis, cardiovascular restenosis, angiographic restenosis, arteriosclerosis, hyperplasia, and other diseases and conditions. For example, the bioactive agent may be selected to inhibit or prevent vascular restenosis, a condition corresponding to a narrowing or constriction of the diameter of the bodily lumen where the stent is placed. The bioactive agent may generally control cellular proliferation. The control of cell proliferation may include enhancing or inhibiting the growth of targeted cells or cell types.

The bioactive agent may include podophyllotoxin, etoposide, camptothecin, a camptothecin analog, mitoxantrone, Sirolimus, and their derivatives or analogs. Podophyllotoxin is an organic, highly toxic drug that has antitumor properties and may inhibit DNA synthesis. Etoposide is an antineoplastic that may be derived from a semi-synthetic form of podophyllotoxin to treat monocystic leukemia, lymphoma, small-cell lung cancer, and testicular cancer. Camptothecin is an anticancer drug that may function as a topoisomerase inhibitor. Related in structure to camptothecin, a camptothecin analog such as aminocamptothecin may be used as an anticancer drug. Mitoxantrone is also an important anticancer drug, used to treat leukemia, lymphoma, and breast cancer. Sirolimus is a medication that may interfere with the normal cell growth cycle and may be used to reduce restenosis. The bioactive agent may also include analogs and derivatives of these agents. Antioxidants may be beneficial on their own rights for their antirestonetic properties and therapeutic effects.

Drug-polymer coating may soften, dissolve or erode from the stent to elute at least one bioactive agent. This elution mechanism may be referred to as surface erosion where the outside surface of the drug-polymer coating dissolves, degrades, or is absorbed by the body, or bulk erosion where the bulk of the drug-polymer coating biodegrades to release the bioactive agent. Eroded portions of the drug-polymer coating may be absorbed by the body, metabolized, or otherwise expelled.

Drug-polymer coating may also include a polymeric matrix. For example, the polymeric matrix may include a caprolactone-based polymer or copolymer, or various cyclic polymers. The polymeric matrix may include various synthetic and non-synthetic or naturally occurring macromolecules and their derivatives. The polymer is advantageously selected in the group consisting of one or more biodegradable polymers in varying combinations, such as polymers, copolymers, and block polymers. Some examples of such biodegradable (also bio-resorbable or else bioabsorbable) polymers include polyglycolides, polylactides, polycaprolactones, polyglycerol sebacate, polycarbonates e.g. tyrosine derived, biopolyesters such as poly(β-hydroxyalcanoate)s (PHAs) and derived compounds, polyethylene oxide, polybutylene terephthalate, polydioxanones, hybrids, composites, collagen matrices with growth modulators, proteoglycans, glycosaminoglycans, vacuum formed SIS (small intestinal submucosa), fibers, chitin, and dextran. Any of these biodegradable polymers may be used alone or in combination with these or other biodegradable polymers in varying compositions. The polymeric matrix preferably includes biodegradable polymers such as polylactide (PLA), polyglycolic acid (PGA) polymer, poly(ε-caprolactone) (PCL), polyacrylates, polymethacryates, or other copolymers. The pharmaceutical drug may be dispersed throughout the polymeric matrix. The pharmaceutical drug or the bioactive agent may diffuse out from the polymeric matrix to elute the bioactive agent. The pharmaceutical drug may diffuse out from the polymeric matrix and into the biomaterial surrounding the stent. The bioactive agent may separate from within the drug-polymer and diffuse out from the polymeric matrix into the surrounding biomaterial. In a further embodiment the drug coating composition may be fashioned using the drug 42-Epi-(tetrazolyl)-Sirolimus, set forth in U.S. Pat. No. 6,329,386 assigned to Abbott Laboratories, Abbott Park, Ill. and dispersed within a coating fashioned from phosphorylcholine coating of Biocompatibles International P.L.C. set forth in U.S. Pat. No. 5,648,442.

The polymeric matrix may be selected to provide a desired elution rate of the bioactive agent. The pharmaceutical drugs may be synthesized such that a particular bioactive agent may have two different elution rates. A bioactive agent with two different elution rates, for example, would allow rapid delivery of the pharmacologically active drug within twenty-four hours of surgery, with a slower, steady delivery of the drug, for example, over the next two to six months. The electro-grafted primer coating may be selected to firmly secure the polymeric matrix to the stent framework, the polymeric matrix containing the rapidly deployed bioactive agents and the slowly eluting pharmaceutical drugs.

The Topcoat Biodegradable Layer

The DES may further comprise a topcoat layer, which can be made from the same composition as that of the biodegradable coating release layer. In particular, the topcoat biodegradable layer may include biodegradable polymers such as polylactide (PLA), polyglycolic acid (PGA) polymer, poly(ε-caprolactone) (PCL), polyacrylates, polymethacryates, or other copolymers.

Manufacturing Process

The electro-grafting of polymers is a technique based on the formation of a polymer layer on a surface in situ, i.e. from a bath of precursors rather than from a pre-made polymer. The surface to be coated is polarized electrically, and serves as a polymerization initiator which provokes surface polymerization via propagation chain reactions (see FR2821575; herein enclosed by reference).

The present invention uses an operational mode in which it is possible to easily carry out an actual electro-grafting of a polymer starting from precursors solutions which are easy to prepare and control, in particular thanks to:
(i) a protocol of application of the electrode potential which forces the reaction of grafting;
(ii) the use of an electrolytic medium which is at least a good swellant of the formed polymer, or even a good solvent of the said polymer.

An adherent film of biocompatible (for example polybutylmethacrylate (p-BuMA)) can be obtained upon voltammetric scanning of a stent (stainless steel, cobalt chromium alloys . . . ) in a solution containing a diazonium salt (especially an aryldiazonium salt, such as 4-nitrobenzenediazonium tetrafluoroborate) at a concentration of $5 \cdot 10^{-4}$ to $10^{-1}$ mol/l (especially $10^{-2}$ mol/l) and the monomer (p-BuMA at 3.5 mol/l) (solvent=DMF), over a potential range of −0.2 V/ECS to −3.0 V/ECS at a scanning rate of 100 mV/s.

The electrolytic solution can include a solvent primarily spectator (i.e. not intervening in the electropolymerisation reaction) intended to solubilize the chain polymerizable monomers. However, monomer(s) may be play the rule of the solvent, rendering the presence of such a liquid not always necessary. When they are used, these solvents are preferably selected among the dimethylformamide, the dimethylsulfoxide, the ethyl acetate, the acetonitrile, the tetrahydrofuranne, the propylene carbonate and other solvents usually used in electrochemistry, dichloroethane and more generally chlorinated solvents. The solvent can also be chosen from the group consisting of water and alcohols. There is not need to subject the solvents to prior distillation in order to eliminate water which they contain, nor to carry out a rigorous control of the water content of the atmosphere above the reaction medium. So the process can easily be implemented on an industrial scale.

The electrolytic solution can also contain at least a supporting electrolyte in order to ensure and/or to improve the passage of the current in the electrolytic solution. When they are used, the supporting electrolytes are preferably selected among quaternary ammonium salts such as perchlorates, tosylates, tetrafluoroborates, hexafluorophosphates, quaternary ammoniums halides, sodium nitrate and sodium chloride. The electrolytic solution can further comprise an agent for improving the homogeneity of the film (a surfactant), such as glycerol.

This film has little crosslinking if any, and that its adhesion on the surface is a result of bond formation with the underlying metal. For this reason, we shall make use of the term electro-grafting of the polymer hereafter, even though it now refers to a grafting that is obtained by the electro-reduction of a solution containing both a monomer that can undergo propagation chain reaction and of a diazonium salt, the latter being preferably at low concentration. Such a process enables the electro-grafting, on all conducting substrates such as stents of organic films, and in particular polymeric, having a thickness going from a few tens of nanometers to a few hundreds of nanometers.

The electro-grafted solution disposed on the stent framework is dried. Excess liquid may be blown off prior to drying the film. Drying of the polymeric solution to eliminate or remove any volatile components may be done at room temperature or elevated temperatures under dry nitrogen or other suitable environment including a vacuum environment. The coated stent may be baked during ~60 min at moderately elevated temperatures on the order of 40° C. under vacuum (~10 mbar) to drive off any solvent trapped inside the primer coating. The thickness of the electro-grafted primer coating may range between 10 nm and 1.0 micron in order to adequately coat the stent framework and to provide a satisfactory underlayer for subsequent drug-polymer application. Additional application and drying steps may be included to reach the desired thickness of the primer coating.

Over the electro-grafted primer coating, a wet process is applied by spray or by dip. The drug polymer may be mixed in a suitable solvent, and applied over the primer using an application technique such as dipping, spraying, painting or brushing. During the coating operation, the drug-polymer adheres well to the electro-grafted primer coating. The drug-polymer coating may be applied immediately after the electro-grafted primer coating is applied. Alternatively, drug-polymer coatings may be applied to a stent with the electro-grafted primer coating at a later time.

A drug polymer may be mixed with a suitable solvent to form a polymeric solution. The drug polymer may include a polymeric matrix and one or more therapeutic compounds. To form a drug-polymer coating, a monomer such as a vinyl acetate derivative may be mixed with other monomers in a solvent such as isopropyl alcohol to form a polymeric solution. The mixture may be reacted to form a polymer, and one or more bioactive agents may be mixed with the polymerized mixture to form a drug polymer with a pre-defined elution rate. A suitable bioactive agent or a solution containing the bioactive agent may be mixed in with the polymeric solution. Alternatively, a polymer such a copolyester or block copolymer may be dissolved in a suitable solvent, and one or more bioactive agents may be added to the mixture. The mixture may be combined with an adhesion promoter in the polymeric solution. One or more adhesion promoters may be selected and added to the mixture.

The polymeric solution may be applied to the stent framework with the electro-grafted primer coating. The polymeric solution may be applied to the stent using any suitable method for applying the polymer solution.

Excess liquid may be blown off and the polymeric solution dried. Drying of the polymeric solution to eliminate or remove any volatile components may be done at room temperature or elevated temperatures (~40° C.) under a dry nitrogen or other suitable environment. A second dipping and drying step may be used to thicken the coating. The thickness of the drug-polymer coating may range between 1.0 microns and 200 microns or greater in order to provide sufficient and satisfactory pharmacological benefit with the bioactive agent.

Treatment of the drug-polymer coating may include air drying or low-temperature heating in air, nitrogen, or other controlled environment. The drug-polymer coating may be treated by heating the drug-polymer coating to a predetermined temperature.

More specifically, illustrative examples of the present invention are provided herein.

The following examples illustrate:
(1) an electro-grafted solution formulation
(2) an electro-grafting process on stainless steel stent
(3) an electro-grafting process on cobalt chromium stent
(4) the corrosion barrier effect of electro-grafted p-BuMA
(5) corrosion barrier properties of electro-grafted p-BuMA and PLA dip coated coupons
(6) a spraying process for the deposition of the reservoir layer
(7) the adhesion enhancement by the electro-grafted layer
(8) Examples of in vitro drug release kinetics
(9) Cytotoxicty study of electro-grafted coatings
(10) Haemolysis study of electro-grafted coatings
(11) Local tolerance study of electro-grafted stents after local implantation
(12) performance of recolonization of electro-grafted BuMA coated stents as compared to BMS, rabbit model at 14 and 28 days;
(13) local tolerance after full coated stent in pigs
(14) Low pressure spray system for the manufacturing of DES with good interface with electro-grafted layers.

Example 1: Electro-Grafting Solution Formulation

One embodiment of the present invention is exhibited by the formulation of an electro-grafting solution based a vinylic monomer n-butylmethacrylate (BuMA) dissolved in a DMF solvent. $NaNO_3$ is used as an electrolyte support.

TABLE 1

| electro-grafting solution formulation | | | | |
|---|---|---|---|---|
| Concentration of vinylic monomer | $DiazoNO_2$ tetrafluoroborate Concentration | $NaNO_3$ concentration | Glycerol | % DMF |
| 30% | $10^{-3}$M | $2.5 \cdot 10^{-2}$M | 5% | 65% |

Example 2: Electro-Grafting Process on Stainless Steel Stents

Using the chemical solution described in example 1, 18 mm stainless steel coronary stent (ClearStream Technologies) were coated with electro-grafted p-BuMA with the following parameters, rinsed and dried for 60 minutes at 40° C. under a 10 mbar vacuum. Using that method the obtained coating thickness is about 150 nm.

Electro-Grafting Parameters:

Method: Cyclic voltammetry from open-circuit potential to −3.2V/CE with argon bubbling (2 Lmin$^{-1}$).
Scan number: 50 scan
Scanning rate: 50 mV/s.

Example 3: Electro-Grafting Process on Cobalt-Chromium Stents

Using the chemical solution described in example 1, 18 mm cobalt-chromium coronary stent (Natec-medical) were p-BuMA electro-grafted with the following parameters, rinsed and dried for 60 minutes at 40° C. under a 10 mbar vacuum. Before the electro-grafting, stent surface is treated by a solution of NH$_4$F 40% for 1 minute. Using that method the obtained coating thickness is about 150 nm.
Electro-Grafting Parameters:
Method: Cyclic voltammetry from open-circuit potential to −3.5V/CE with argon bubbling (2 Lmin$^{-1}$).
Scan number: 50 scan
Scanning rate: 50 mV/s.

Example 4: Corrosion Barrier Properties of Electro-Grafted p-BuMA

The anticorrosion potential of electro-grafted p-BuMA is assessed on coated stainless steel coupons synthesized according to the protocol described in example 2.

For this purpose, electro-grafted p-BuMA coated coupons (assay) and non coated coupons (control) are immersed in a NaCl solution, at 9 g/l according to a ratio surface area/volume of 1 cm$^2$/ml. The samples are kept at 37° C. under gentle stirring and the time course of cobalt, nickel and molybdenum ions liberation is assessed by regular sampling of release medium. The ions are quantified using Inductively Coupled Plasma-Mass Spectrometer (ICP-MS).

TABLE 2

| | ion release | | |
|---|---|---|---|
| | Ion release (ng/cm$^2$) in a 9 g/l NaCl solution at 37° C. during 150 days | | |
| | Ni | Cr | Mo |
| BMS 316L | 28 | 12 | 8 |
| p-BUMA (150 nm) on BMS 316L | 3 | 7 | 1 |

The ion release from the metallic surface is strongly reduced by the electro-grafted p-BuMA coating for example the released nickel (which is by far the most toxic element) decreases from 28 ng/cm$^2$ for the stainless steel coupons to 3 ng/cm$^2$ for the electro-grafted p-BuMA coupons.

Example 5: Corrosion Barrier Properties of Electro-Grafted p-BuMA and PLA Dip Coated Coupons Stainless steel electro-grafted p-BuMA coupons are dip coated in a polylactide (p-PLA) solution (5% w/v in chloroform) containing or not 20% (w/w) of a model drug, pentoxifylline. After the dipping, the coatings are stabilized at room temperature for 24 hours and dried in an oven at 40° C. for 48 hours. The ion release is performed according to the protocol described in example 3. A comparison of Cr(A), Ni(B) and Mo(C) ions release from 316 stainless steel coupons, electro-grafted p-BuMA+p-PLA dip coated and electro-grafted p-BuMA+p-PLA dip coated coupons containing pentoxifylline, in NaCl (9 g/l) solution at 37° C. during 150 days is given in the table 3 below:

TABLE 3

| | Ion release at 150 days (ng/cm$^2$) | | |
|---|---|---|---|
| | Cr | Ni | Mo |
| Inox | 18 | 30 | 8 |
| Inox + PLA | 6 | 8 | 1 |
| Inox + PLA + PTX | 4 | 7 | 1 |

The same decrease of ions release is observed on stainless steel coupons coated with the double layered coating, the amount of Ni ions drop dramatically from 30 ng/cm$^2$ to about 8 ng/cm$^2$ as well as the Cr ions amount which decrease from 18 ng/cm$^2$ to 6 ng/cm$^2$ and 4 ng/cm$^2$ respectively for the electro-grafted p-BuMA/p-PLA coating and electro-grafted p-BuMA/PLA/pentoxifylline coating.

Example 6: Spray Coating Process

A spray coating process for disposing a reservoir polymer coating on an electro-grafted metallic stent exhibits another embodiment of the present invention. After drying, an 18 millimeter electro-grafted stent is spray coated with biodegradable polyester (polylactide-co-glycolide 50/50, PLGA) containing Sirolimus.

The copolymer (0.25% w/v) is dissolved in chloroform. Sirolimus is then dissolved in the chloroform/polymer mixture to obtain a final ratio Sirolimus/polymer of 30% (w/w). The mixture is applied to the electro-grafted p-BuMA stent, mounted on rotative mandrel, by spraying with a fine nozzle with the following parameters:

TABLE 4

| spraying parameters | |
|---|---|
| Spraying flow (µL/s) | 24 |
| Spray volume (µL) | 192 |
| Pressure (bar) | 0.3 |
| Stent rotation speed (rpm) | 2000 |
| Nozzle/stent distance (mm) | 6.5 |
| Number of spray run | 50 |

The two layered coating is applied to both the luminal and abluminal sides of the stainless steel stent, with a higher (and tunable) thickness on the abluminal surface with respect to the luminal surface. Drying at 40° C. is performed in a vacuum oven. Using the above parameters, the coating on the stent, weighs 800+/−80 µg, and the coating thickness is about 5 to 7 µm. The drug loading is 164+/−16 µg.

Example 7: Enhancement of Reservoir Polymer Adhesion by Electro-Grafted p-BuMA Underlayer; a Functional Testing An adhesion test is run to highlight the adhesion strength of the reservoir polymer layer on the pre-electro-grafted stent. The double layer coating on stainless steel stents (18 mm, Clearstream Technologies) is achieved in accordance with examples 1 and 6.

The test is run to simulate the abrasion that a coating might experience during the implantation. For that purpose, the coated stent is passed several times through a silicon tube that mimics a coronary artery, after which the stent is deployed. The test is followed by optical and scanning electron microscope inspection of the stents.

No coating delamination is observed for primer electro-grafted stents: all the 10 electro-grafted-coated stents pass the simulated lesion abrasion test whereas the spray coated stents without the electro-grafted p-BuMA primer exhibit severe delamination.

Example 8: In Vitro Drug Release Study

In this embodiment, the time course release of Sirolimus from a double layer coated stent is achieved according to the following protocol:

18 mm stainless steel stents are coated according to the protocols given in example 1 for the electro-grafted p-BuMA and example 5 for the biodegradable polymer spray coating. Each coated stent is immersed in a vial containing 1 ml of a release solution (99% phosphate buffer 0.01M, pH=7.4/1% Tween 20) and kept at 37° C. under a gentle sitting. The release medium is removed regularly and replaced by fresh one. Absorbance (Arbitrary units) is measured using a spectrophotometer Hitachi 3 at $\lambda$=278 nm wavelength against the release medium.

Sirolimus concentration is determined, in triplicate, using a calibration curve.

Figure 1B:
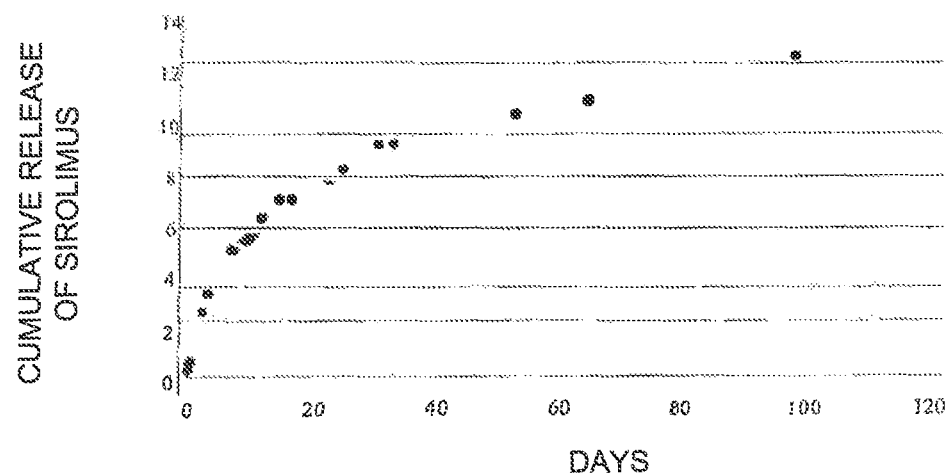
FIG. 1(B) shows the cumulative release of Sirolimus over the time (days) from a double layer coating of poly(lactide), in vitro.

The FIGS. 1(A) and 1(B) illustrates respectively a fast release (A) and a slow release (B) of Sirolimus from a double layer coating in vitro (cumulative release (%) versus time (days)). For the fast release, the reservoir layer is a copolymer (50/50) of lactide and glycolide, PLGA (120 000 g/mol), whereas for the slow release the biodegradable polymer is a poly(lactide) (30 000 g/mol).

The difference in drug release kinetic is directly related to the degradation rate of the biodegradable reservoir layer. Since the 50/50 PLGA polymer degrades faster than the PLA.

Figure 2:
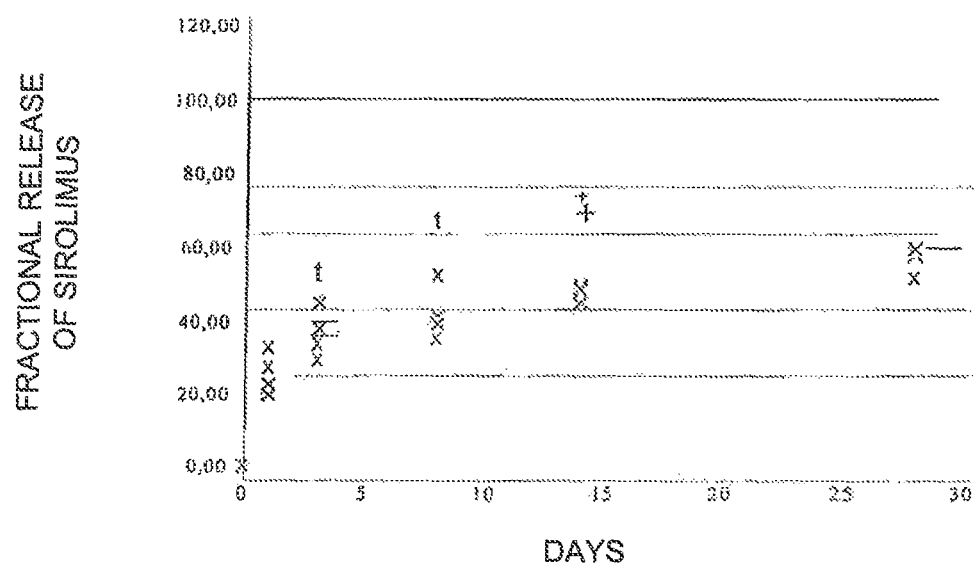
FIG. 2 shows the fractional release of Sirolimus over the time (days) from PLGA or PLA, in vivo.

The corresponding profiles in vivo, obtained from the measurement of residual drug on the explanted stents from NZ rabbits in an iliofemoral model, are shown in FIG. 2 (fractional release over the time (days):

+ profile is that of PLGA
× profile is that of PLA.

The drug released (Sirolimus) and the loading were the same in the two cases.

This figure shows that the drug is fully released and the release polymer has fully disappeared at 28 days for the fast release (PLGA) while the drug release is only of 60% at 28 days with PLA, which is thought to disappear over 2 months.

Example 9: Cytotoxicity Study of Electro-Grafted Coatings

A potential cytotoxicity study of the electro-grafted coatings is conducted in accordance with the standard ISO 10993-5.

The study intended to qualitatively and quantitatively assess the cytotoxicity of the electro-grafted p-BuMA tested as an extract, after application to cells seeded in 96-well microplate.

The extraction was performed in triplicate with the culture medium (DMEM) containing fetal calf serum, in sterile, closed, chemically inert containers during 96 h at 37° C. The ratio between the surface area of electro-grafted p-BuMA and the volume of extraction vehicle was equal to 3 $cm^2$/ml.

The extract and its dilutions (50% and 10%) were placed on the cells and left in contact for 24 hours, at least. The cytotoxicity was determined by a vital dye, the neutral red.

The means of determination retained were the general morphology of the cell (qualitative evaluation) and the percentage of cell viability (quantitative evaluation) based on that the absorbance obtain by reading at 540 nm, is proportional to the number of living cells (quantitative analysis).

Positive control; the control was performed for each test with a product which provided a reproducible cytotoxic effect under the conditions of the test: a solution of phenol at 3.2 g/l in culture medium (DMEM). The test complied if the percentage of mortality was about 100%.

Negative control: The control is performed with a material (high density polyethylene) which produced no cytotoxic effect under the conditions of the test. The test complied if the percentage of cell viability is 100%.

TABLE 5

Qualitative and quantitative evaluation of cytotoxicity of electro-grafted p-BuMA primer

| Samples | | Qualitative evaluation | Absorbance at 540 nm | Viability % | Death % |
| --- | --- | --- | --- | --- | --- |
| DMEM control | | All the cells are colored by neutral red | 0.495 ± 0.016 | 100% | 0% |
| Extraction solvent | | All the cells are colored by neutral red | 0.521 ± 0.028 | 100% | 0% |
| Extract 1 | 100% | All the cells are colored by neutral red | 0.514 ± 0.019 | 100% | 0% |
| | 50% | | 0.520 ± 0.007 | 100% | 0% |
| | 10% | | 0.511 ± 0.030 | 100% | 0% |
| Extract 2 | 100% | All the cells are colored by neutral red | 0.497 ± 0.012 | 100% | 0% |
| | 50% | | 0.507 ± 0.028 | 100% | 0% |
| | 10 | | 0.517 ± 0.013 | 100% | 0% |
| Extract 3 | 100% | All the cells are colored by neutral red | 0.501 ± 0.036 | 100% | 0% |
| | 50% | | 0.505 ± 0.041 | 100% | 0% |
| | 10 | | 0.506 ± 0.023 | 100% | 0% |
| Negative control | | All the cells are colored by neutral red | 0.479 ± 0.012 | 97% | 3% |
| Positive control | | Cells don't incorporate the neutral red | 0.007 ± 0.002 | 1% | 99% |

The test performed on the extracts of electro-grafted primer coating shows no evidence of cell toxicity after twenty-four hours.

Example 10: Haemolysis Study; Direct Contact Tests

Haemolysis, in this example, refers to the breakdown of red blood cells in direct contact with electro-grafted coatings. The haemolysis study is carried out on 1 cm² electro-grafted p-BuMA and sterilized stainless steel coupons in accordance with ISO 10 993-4 and ASTM F 756-93.
Reparation of Human Blood Substrates:
Citrate anticoagulated human blood is obtained in sterile conditions from three donors. Blood is used within 1 hour.
Dilution of Blood Substrates:
Hemoglobin concentration of each blood is assessed and was 97.95±8.32-111.86±3.90-91.05±0.94 mg/ml.
Free plasma hemoglobin has to be lower than 1 mg/ml (0.30-0.32-0.28 mg/ml).
The total hemoglobin content of each blood sample is adjusted to 25.01±2.5 mg/ml by diluting by an appropriate amount of normal saline (25.66±0.05 mg/ml-26.19±1 mg/ml-25.37±0.69 mg/ml).
Hemoglobin Determination:
Blood hemoglobin: 20 µl of blood are mixed with 5 ml of Drabkin's reagent (Sigma-525-2) (15 minutes). Absorbance (Arbitrary Units) is measured using a spectrophotometer at $\lambda=540$ nm. Hemoglobin concentration is determined using a calibration curve from 0.036 to 0.72 mg/ml prepared using a reference standard (Hemoglobin standard, Sigma-525-18).
Plasma hemoglobin: 100 µl of plasma are mixed with 5 ml of Drabkin's reagent in hemolysis tube (15 minutes). Absorbance (Arbitrary units is measured using a spectrophotometer (Kontron) at $\lambda=540$ nm wavelength against Drabkin's reagent.
Hemoglobin concentration is determined in triplicate using a calibration curve from 0.036 to 0.720 mg/ml, prepared using a reference standard (Hemoglobin standard, Sigma-525-18).
Static Tests:
In sterile conditions, 5 ml of each of the blood substrate are transferred in screw-cap test tubes containing the test material. The ratio between the surface area of test material samples and the volume of the blood substrates is 3 cm²/ml. The positive control is constituted of 200 µl of blood substrate supplemented of 10 ml of water.
The negative control is constituted of blood substrate alone.
Tubes are capped and maintained stationary in a suitable test tube rack for 4 h at 37° C. At the end of the specified incubation time, all tubes are centrifuged (100×G, 15 min). Each supernatant cell-free plasma fraction is transferred to 15 ml tube (polypropylene, sterile) and centrifuged (700×G, 5 min). Supernatants are carefully removed for subsequent hemoglobin analysis.
Hemoglobin determination: 1 ml of supernatant is mixed with 3 ml of Drabkin's reagent. Absorbance is measured at $\lambda=540$ nm. A calibration curve from 0.03 to 0.72 mg/ml is prepared using a reference standard (hemoglobin standard, Sigma-525-18).
Plasma hemoglobin concentration is determined in each supernatant using the calibration curve.
Hemolytic index (HI) is calculated according to the following formula:

HI (%)=(Free hemoglobin in the supernatant/Total hemoglobin present in the blood substrate)×100

The table 6 presents hemoglobin level in supernatants and table 7 gives the corresponding hemolytic index (HI). The average HI obtained for the negative control using 3 bloods, assessed in triplicate, is 0.35±0.04%. The average HI in the presence of the p-BuMA primer using 3 bloods, assessed in triplicate, is 0.29±0.03%.

TABLE 6

Hemoglobin level in the supernatants
Hemoglobin (mg/ml)

|  | Positive control | Negative control | electro-grafted p-BuMA samples |
|---|---|---|---|
| S1 (substrate) | 25.66 ± 0.05 | 26.60 ± 0.11 | 0.09 ± 0.01 | 0.06 ± 0.01 |
| S2 (substrate) | 26.19 ± 1.00 | 26.72 ± 0.18 | 0.08 ± 0.01 | 0.08 ± 0.00 |
| S3 (substrate) | 25.37 ± 0.69 | 25.79 ± 0.33 | 0.10 ± 0.01 | 0 08 ± 0.01 |

TABLE 7

Hemolytic index
Hemolytic index (HI)

|  | Positive control | Negative control | electro-grafted p-BuMA samples |
|---|---|---|---|
| S1 (substrate) | 103.68 ± 0.43 | 0.35 ± 0.04 | 0.25 ± 0.04 |
| S2 (substrate) | 102.01 ± 0.67 | 0.31 ± 0.05 | 0.31 ± 0.00 |
| S3 (substrate) | 101.67 ± 1.30 | 0.39 ± 0.03 | 0.31 ± 0.03 |

The results indicate that electro-grafted-coated samples have no hemolytic properties in direct contact.

Example 11: Local Tolerance after Electro-Grafted Stent Implantation in Rabbits

The objective of this study was to evaluate the local tolerance of a electro-grafted p-BuMA stent as compared to a bare metal stent. The electro-grafted coated stents (stainless steel, 18 mm length) are coated according to the protocol given in EXAMPLE 2 and sterilized by ethylene oxide using a validated standard protocol (43° C., 50% of relative moisture).
Experimental Procedure
1—Implantation Site
Each animal was implanted in the right and/or left iliac artery site with the coated or non coated stent for 4 weeks.
2—Animal Preparation and Anesthesia
The rabbits were premedicated with atropine (atropinum sulfuricum, AGUETTANT, France), anesthetized with tiletamine-zolazepam (Zoletil® 100, VIRBAC, France) 25 mg/kg and xylazine (Rompun® 2% BAYER AG, Germany) 5 mg/kg, by intramuscular route according to the internal standard procedure. The surgical sites were clipped free of fur, scrubbed with a germicidal soap (Vetedine® savon, VETOQUINOL, France) and disinfected with povidone iodine (Vetedine® solution, VETOQUINOL, France).
The following treatment was administered into the femoral artery through the introducer before implantation of each stent:
Aspegic® (SYNTHBLABO, France), 50 mg.
Heparine Choay® (SYNTHELABO, France), 50 IU.

Moreover, before each angiography the following vasodilating treatment was administered into the femoral artery:
Corvasal® (linsidomine, 0.06 mg, AVENTIS, France).

3—Pre-Procedural Angiography

One carotid artery was exposed and a 5 or 6 Fr introducer sheath was introduced. A 5 or 6 guiding catheter and a Guide Wire (GW) were advanced through the sheath to the terminal aorta. An angiographic mapping of the iliac vascular tree was performed by injection of contrast material (Hexabrix® 320, Laboratoires GUERBET, France) with Philips BV212 equipment. The diameter of each artery was recorded. The targeted overstretch following stent implantation was approximately 1.2.

4—Placement of the Stent

The stent was implanted in the iliac arteries (1 or 2 stents per animal) according to the following procedure:
Insertion of a guiding catheter (GC) and GW into the target site.
Full retraction of the GW.
Insertion of the stent deployment system into the target site.
Deployment of the stent under a defined balloon pressure (=8 atmospheres).
Implantation of the stent in the common iliac artery.
Delivery system withdrawal from the GC.

5—Post-Procedural Angiography

An immediate evaluation of the patency of the implanted arteries was performed by angiography. The diameter of each artery was recorded and the obtained overstretch was calculated.

6—Pharmacological Treatment and Observation Period

Animals were observed daily for any clinical abnormality. Anticoagulant treatment began one day before the implantation procedure and was administered on a daily basis for 30 days: Aspegic® (aspirin 100 mg/ml, SYNTHELABO, France), intramuscular, 50 mg/day.

7—Sacrifice and Sampling

Animals were sacrificed by lethal injection of barbiturate (Dolethal$^{ND}$, Labortoires VETOQUINOL, France). A gross examination of the external surface of the implanted arteries was performed: any local intolerance criteria (inflammation, necrosis, hemorrhage or any other lesion) was observed and recorded. Macroscopic photographs were performed. Samples were identified and fixed in 10% buffered formalin solution for histopathology.

8—Histopathologic Sample Preparation

Implanted sites were dehydrated in alcohol solutions of increasing concentrations and embedded in PMMA (polymethylmetacrylate). One distal section was obtained by a microcutting and grinding technique adapted from Donath (Donath K., Brunner G.: A method for the study of undecalcified bone and teeth with attached soft tissues. J. Oral. Pathol., 11; 318-326, 1982). The section was stained with modified Paragon staining for qualitative and quantitative analysis.

9—Interpretation

Histological slides were examined under light microscopy (NIKON Eclipse E600, fitted with ×4, ×10, ×20 and ×40 lenses, coupled with a digital camera DN 100 NIKON). A semi-quantitative histological evaluation was performed according to the ISO 10993-6 standard. Particular attention was devoted to the presence of fibrous tissue, fibrin, degenerative phenomena, necrosis, smooth muscle cells, elastic lamina distension, inflammatory cells and material degradation and thrombus presence.

Histological micrographs were performed. Each parameter was graded according to the following grading scale:
0: absent
1: limited
2: moderate
3: marked
4: severe These parameters allowed an accurate evaluation of any inflammation, foreign body reaction, and immunologic reaction. Neointimal formation was qualitatively assessed.

Results

1—Hispathological Analysis

The semi-quantitative analysis is reported in table?.

2—General Observations

The stent struts showed a square shape with rounded angles. No microscopic stent material alteration was observed in the specimens.

3—Non Coated Stents (Control Article)

All the stents were fully deployed and well integrated in the vascular wall. The stent frame was integrated into a neointimal tissue of moderate thickness containing a moderate number of smooth muscle cells, fibrocytes and a limited infiltration of macrophages. One sample (animal n° 3 right) showed limited elastic lamina rupture without medial protrusion. The presence of limited amount of proteoglycan substance was suspected within the neointimal tissue of one sample (animal n° 11 left). No thrombus was observed.

4—Coated Stents (Test Article)

The thickness of the fibromuscular neointimal layer covering the stent frame was comparable to or slightly thinner than in the reference group. This finding was obtained by intra-animal comparison. Due to the limited number of samples and evaluable observations no conclusion concerning the biological significance of the findings can be drawn. The macrophagic reaction was of slight magnitude similar to the reference group. No thrombus was observed.

A total of 10 out of 14 animals were successfully implanted with the coated (test article) and/or the non coated stent (control article). The artery overstretch after stenting reached approximately 1.1 to 1.4 times the initial artery diameter in this study. After 1 month of implantation, no visible macroscopic lesions (necrosis, inflammation, hemorrhage) were identified in the specimens retrieved from the 8 surviving animals (n=6 non coated stents; n=7 coated stents). No sign of occlusion was observed at sacrifice.

TABLE 8

Semi quantitative histopathological analysis

| Implanted device | Animal n° | Iliac site | Elastic lamina distension | Mural thrombus | Fibrin deposit | Necrosis | Tissue degeneration | Polymorphonuclear cells (PMN) | Lymphocytes |
|---|---|---|---|---|---|---|---|---|---|
| Test | 1 | L | 2 | 0 | 0 | 0 | 0 | 0 | 0 |
|  | 2 | R | 2 | 0 | 0 | 0 | 0 | 0 | 0 |
|  | 3 | L | 2 | 0 | 0 | 0 | 0 | 0 | 0 |

TABLE 8-continued

Semi quantitative histopathological analysis

|  |  |  |  |  |  |  |  |  |  |
|---|---|---|---|---|---|---|---|---|---|
|  | 4 | R | 2 | 0 | 0 | 0 | 0 | 0 | 0 |
|  | 11 | L | 2 | 0 | 0 | 0 | 0 | 0 | 0 |
|  | 12 | R | 2 | 0 | 0 | 0 | 0 | 0 | 0 |
|  | 14 | R | 2 | 0 | 0 | 0 | 0 | 0 | 0 |
|  |  | M |  | 0 | 0 | 0 | 0 | 0 | 0 |
| Control | 3 | R | 3 | 0 | 0 | 0 | 0 | 0 | 0 |
|  | 4 | L | 2 | 0 | 0 | 0 | 0 | 0 | 0 |
|  | 7 | R | 2 | 0 | 0 | 0 | 0 | 0 | 0 |
|  | 11 | R | 2 | 0 | 0 | 0 | 0 | 0 | 0 |
|  | 12 | L | 2 | 0 | 0 | 0 | 0 | 0 | 0 |
|  | 14 | L | 2 | 0 | 0 | 0 | 0 | 0 | 0 |
|  |  | M | 2.2 | 0 | 0 | 0 | 0 | 0 | 0 |

| Implanted device | Animal n° | Iliac site | Plasma cells | Macrophages | Giant cells | Fibrocytes | Neointimal proliferation | Smooth muscle cells | Integration | Arterial wall protrusion |
|---|---|---|---|---|---|---|---|---|---|---|
| Test | 1 | L | 0 | 1 | 0 | 2 | 2 | 2 | 4 | 0 |
|  | 2 | R | 0 | 2 | 1 | 2 | 2* | 2 | 4 | 0 |
|  | 3 | L | 0 | 1 | 0 | 2 | 2 | 2 | 4 | 0 |
|  | 4 | R | 0 | 1 | 0 | 1 | 1 | 1 | 4 | 0 |
|  | 11 | L | 0 | 1 | 0 | 1 | 1 | 1 | 4 | 0 |
|  | 12 | R | 0 | 2 | 0 | 2 | 2 | 2 | 4 | 0 |
|  | 14 | R | 0 | 1 | 0 | 1 | 1 | 1 | 4 | 0 |
|  |  | M | 0 | 1.3 | 0. | 1. | 1.6 | 1. | 4. | 0 |
| Control | 3 | R | 0 | 1 | 0 | 2 | 2 | 2 | 4 | 0 |
|  | 4 | L | 0 | 1 | 0 | 1 | 1 | 1 | 4 | 0 |
|  | 7 | R | 0 | 1 | 0 | 1 | 1 | 1 | 4 | 0 |
|  | 11 | R | 0 | 1 | 0 | 2 | 2 | 2 | 4 | 0 |
|  | 12 | L | 0 | 1 | 0 | 2 | 2 | 2 | 4 | 0 |
|  | 14 | L | 0 | 1 | 0 | 2 | 2 | 2 | 4 | 0 |
|  |  | M | 0 | 1 | 0 | 1. | 1.7 | 1. | 4. | 0 |

R = Right;
L = Left;
M = Mean

Results of histological sections of rabbit retrieved stent after 1 month of implantation: no signs of local intolerance reaction for all the test or control stent series and comparable results in terms of stenosis with the presence of a mild fibromuscular neointimal proliferation Conclusion The main histopathological findings were as follows:

All the test and control stents were fully deployed and well-integrated in the vascular wall with no thrombus.

After one month implantation, no signs of local intolerance reaction were observed for all the test or control stent series.

The test and control stent series showed comparable results in terms of stenosis with the presence of a mild fibromuscular neointimal proliferation.

In addition, electro-grafted layers are capable of preventing the cracking and delamination of biodegradable polymer layers, and show equal if not better recolonization than stainless steel bare metal stents in the rabbit model (ISO 10993).

Example 12: Recolonization at 14 and 28 Days in Rabbits on p-BuMA Electro-Grafted Stents as Compared to BMS Cobalt chromium stents were coated with a ca. 200 nm electro-grafted p-BuMA layer following the protocol of example 3. Ten New Zealand white rabbits underwent placement of 20 stents (18 mm, bare metal, n=10, and coated with electro-grafted p-BuMA layer, n=10) in the iliofemoral arteries, under general anaesthesia.

A first group of 5 animals were euthanized at 14 days, and then a second group at 28 days. The iliofemoral arteries were extracted and worked out to perform longitudinal cross sectioning, according to the protocol described in Finn et al., Circulation, 112, 270 (2005). The cross sections were examined by SEM and the endothelial coverage was estimated from the SEM pictures (ibid.).

The results are summarized in the tables 9 and 10 below:

TABLE 9

| endothelial coverage (%) from SEM longitudinal cross sections, over struts | | |
|---|---|---|
|  | 14 days | 28 days |
| BMS | 98% | 93% |
| p-BUMA on BMS | 88% | 100% |

TABLE 10

| endothelial coverage (%) from SEM longitudinal cross sections, in between struts | | |
|---|---|---|
|  | 14 days | 28 days |
| BMS | 98% | 93% |
| p-BUMA on BMS | 89% | 100% |

These results show that both over struts and in between the struts, the endothelial coverage (as measured from SEM analysis of the longitudinal cross sections) is superior or equivalent on the stents coated with an electro-grafted p-BuMA layer as compared to the Bare Metal Stent. One shall note in particular that the recolonization is effective as early as 14 days after implantation for the electro-grafted stents, which shows that optimal stents based on this technology should benefit from this effect and reduce the drug release period to the minimum in order to facilitate the pro-healing effect.

Example 13: Local Tolerance after Full Coated Stent in Pigs

A 60 day pig trial has been conducted with a composite layer made of an electro-grafted p-BuMA underlayer (150 nm) overcoated with a PLGA (poly-lactide-co-glycolide) biodegradable release layer (5 µm). Briefly, sixteen domestic male pigs (25 to 30 kg) underwent placement of 32 stents (18 mm length, bare-metal, n=16 and double layer coated stents, n=16) in the left anterior descending (IVA) or, left circumflex coronary arteries (Cx) under general anaesthesia.

A segment with a mean coronary diameter of 2.5 mm is selected by using quantitative coronary angiography with a stent-to-artery ratio of approximately 1.2. A balloon catheter mounted with a stent is then advanced to the pre-selected coronary segments for deployment over a standard guide wire. The balloon catheter is inflated at 10 atm for 10 seconds once and is then slowly withdrawn, leaving the stent in place (no pro- or post-dilatation).

Coronary IVUS:

To assess the extent of neointimal formation in vivo, the IVUS was performed 8 weeks after the stent implantation.

Artery Sampler:

The heart is excised 8 weeks after stent implantation. IVA, Cx and CD are removed, rinsed in phosphate-buffered saline (PBS) then prepared as indicated for histomorphometry, immunochemical analysis, or electron scanning microscopy.

Histomorphometry

Samples are fixed in formalin (3%) at 4° C. for 12 h, dehydrated in graded ethanol series (70° to 100° at 4° C.) and acetone for 24 h, then embedded in glycomethylmetacrylate (GMA). For each sample, 50 µm-thick sections are cut (Isomet, Buehler France) and stained with Verhoeff-van Gieson for analysis. Histological sections are observed (Nikon E-600, Nikon, France), digitized, and morphometry measurements are performed (Metamorph, France). Neointimal thickening is quantified by morphometric analysis, made in 5 sections for each artery segment. Neointimal area is measured as the area from the internal elastic lamina (IEL) to the luminal border, and media area as the area between the IEL and the external elastic lamina. Neointimal thickening as expressed as the ratio [(neointimal area/neointimal area+ media area)].

Immunochemical Analysis

At the end of the dessication process, stents are removed and arteries are embedded in paraffin blocks that are cut into 4 µm-thick sections and then immersed in a 3% hydrogen peroxide aqueous solution (Sigma, France) to inhibit endogenous peroxidase activity. Non-specific staining is blocked by 10-min incubation in 5% bovine albumin PBS. After two washes in PBS, sections are incubated in various antibodies (antiMIB1, α-actin, factor VIII, macrophages (AM-3K)). Two independent observers count stained cells in neointima and media areas.

Scanning Electron Microscopy

For this purpose, samples are fixed with 4% glutaraldehyde, 0.1M phosphate buffer, PH 7.2 for 1 h at 4° C., and washed in PBS for 1 h. Next they are dehydrated through a graded ethanol and pure acetone, and critical-point dried from $CO_2$ (CPD 010 BAL-TEC AG, Liechtenstein). Specimens are sputter-coated with Au/Pd (Emscope Ashford UK) for scanning electron microscopy (JSM 6300 Jeol Tokyo Japan) observation with secondary electrons.

2.8. Statistical Analysis

All experiments are done in triplicate, and results are expressed as the mean±SD. An ANOVA test is performed on these values (p<A preparation by antiplatelet therapy (Plavix 300 Mg and aspirin 75 Mg) is started the day before of the catheterization and is continued during all the duration of the study (6 hours, 1 month and 2 months follow-up) to the usual amounts (Plavix 75 mg and aspirin 75 mg per day). The pigs are catheterized by femoral way into 6 french under radioscopy (Seldinger). A probe "EBU" (Medtronic) is placed at ostium of the left coronary trunk and allows a selective opacification of the coronary network. After injection of 50 heparin UI/kg, an initial endocoronary echographic control (IVUS) is carried out (Atlantis Plus 40 mhz, Boston). The initial IVUS makes it possible to estimate the diameter of the coronary artery and to guide the stent implantation to obtain a ratio stent/artery of 120%. A stent is then placed in the average segment of the vessel (12 atm. 10 dryness). After a new coronarographic control and IVUS to ensure of the good apposition of the stent, the whole of the material is withdrawn and a manual compression is exerted on the point of femoral puncture until obtaining the hesmostasis. After two months of life, a new catheterization is carried out as described above for a coronarographic control. The evaluation of the intra-stent stenosis and the neointimal proliferation is performed by a new IVUS.

The study could first show that the biodegradable release layer had disappeared after the first 4 weeks, hence releasing 100% of the drug. Indeed, by SEM one only sees the "rough" electro-grafted p-BuMA layer characterized by its "lunar" aspect (reproducible "crater" surface irregularities; though it is homogeneous and has polymer everywhere, even in the "lunar holes"). Observing by SEM the surface of a stent explanted 30 days after implantation, one sees the "lunar craters" characteristic of the electro-grafted p-BuMA, evidencing the full disappearance of the biodegradable layer, and hence the total release of the drug. The disappearance of the biodegradable layer is further confirmed by ToF-SIMS analysis on both the above surface and that of the inside of the artery, which reveal the absence of the drug of the biodegradable polymer.

In view of the recolonization observations at 8 weeks, the electro-grafted p-BuMA is prone to proper recolonization by endothelial cells.

The IVUS results demonstrate a very good tolerance of the double layer coated stents, since after 8 weeks implantation very low amount of neotimal proliferation was observed, this is confirmed by the immunohistological studies which demonstrate that the coating is very safe with no inflammation as shown by HES staining, a complete endothelization von-(willebrand staining) and a very little amount of smooth muscle cell proliferation.

Example 14: "Low Pressure" Spray System for the Manufacturing of DES with Good Interface with Electro-Grafted Layers The machine is made of a glove box with one transparent wall. A X-Y scanning system is placed on top of it outside of the box, and moves a magnet on the outside, which further handles the X-Y movement of another magnet on the ceiling of the inside of the box. The latter inside magnet is further connected to a nozzle.

The far wall of the box has a male appendix which is connected to an outside electrical engine, enabling the rotation of the appendix at a speed controllable from the front panel of the machine by adjustment of the voltage of the said engine.

Stents are placed on needles, which are further plugged onto tips on the sampleholder. These tips can all rotate relative to the sampleholder: they are connected to a common rotating stick inside the sampleholder, which ends up—at the rear of the sampleholder—with a female appendix which can plug onto the male appendix in the far wall of the box. Hence, when all stents are placed on the needles which are themselves plugged onto the tips, and when the sample holder is plugged onto the far wall of the box, all stents rotate simultaneously and at the same tunable speed.

The X-Y system is piloted via an external computer, and drives the sequence of movements and sprays of the nozzle, which is placed on top of each and every stent, one after the other, starts spraying while moving along the whole stent length, one way and one way back, before stopping the spray to move to the next stent and starts spraying again. The sample holder can hold 20 stents per batch, so that the nozzle is displaced from stent #20 back to stent #1 for a second sequence of spray: each stent basically "sees" no spray for a period corresponding to 19 times the time $T_S$ to spray one stent+the one time the time $T_O$ to sweep the nozzle over the entire length of the sample holder. All stents thus see exactly the same protocol, and the coating unit turns out to be very reproducible.

Mass deviation results (mass of the coating on a series of 53 DES which have been sprayed using the machine described above) show that with an acceptance criterion of 15% relative to the target mass (and hence to the target drug dose), only 3 DES are rejected for being out of specs, giving a total yield of 94.2%. Even if a tighter 10% tolerance is applied, the system affords a yield of 86.5%, which is substantially higher than with most existing industrial systems (for which usual specs are within ca. 20% on the drug dose).

We attribute this quality to the very high reproducibility of the wet/low pressure system, which is ideally promoted thanks to the wetting offered by the appropriate electrografted layer. We have also experienced that for a low pressure, gas driven, nozzle, the correlation between the concentration of drug in the spraying solution and that in the polymer layer at the end is very linear and very reproducible, even though it is not a strict one-to-one correlation.

What is claimed is:

1. A drug-eluting stent, comprising:
   a stent framework;
   an electro-grafted polymeric layer disposed on the stent framework; and
   a drug-containing biodegradable polymeric layer disposed on said electro-grafted polymeric layer;
   wherein said drug-containing layer and said electro-grafted polymeric layer are interpenetrated, forming an interdigitated interface without chemical bonding or layering;
   and wherein said drug-containing biodegradable polymeric layer comprises a mixture of polymers with one or more drugs.

2. The drug-eluting stent of claim 1, wherein the stent framework comprises a metallic base.

3. The drug-eluting stent of claim 1, wherein the electro-grafted polymeric layer has a thickness between 10 nm and 1.0 micron.

4. The drug-eluting stent of claim 1, wherein the electro-grafted polymeric layer is made from a monomer selected from the group consisting of vinylics, epoxides, and cyclic monomers undergoing ring opening polymerisation and aryl diazonium salts.

5. The drug-eluting stent of claim 4, wherein the monomer is selected from the group consisting of butyl methacrylate, methyl methacrylate, hydroxyethyl methacrylate, epsilon caprolactone, and 4-aminophenyl diazonium tetrafluoro borate.

6. The drug-eluting stent of claim 1, wherein the drug-containing biodegradable polymeric layer hosts a bioactive agent.

7. The drug-eluting stent of claim 6, wherein the bioactive agent is selected from the group consisting of an antisense agent, an antineoplastic agent, an antiproliferative agent, an antithrombogenic agent, an anticoagulant, an antiplatelet agent, an antibiotic, an anti-inflammatory agent, a gene therapy agent, a therapeutic substance, an organic drug, a pharmaceutical compound, a recombinant DNA product, a recombinant RNA product, a collagen, a collagenic derivative, a protein, a protein analog, a saccharide, and a saccharide derivative.

8. The drug-eluting stent of claim 6, wherein the drug-containing biodegradable polymeric layer comprises polymers selected from the group consisting of one or more biodegradable polymers, copolymers, and block polymers.

9. The drug-eluting stent of claim 8, wherein the biodegradable polymer is selected from the group consisting of polyglycolides, polylactides, polycaprolactones, polyglycerol sebacate, polycarbonates, e.g., tyrosine derived, biopolyesters, such as poly($\beta$-hydroxyalcanoate)s (PHAs) and derived compounds, polyethylene oxide, polybutylene terephthalate, polydioxanones, hybrids, composites, collagen matrices with growth modulators, proteoglycans, glycosaminoglycans, vacuum formed small intestinal submucosa, fibers, chitin, dextran, and mixtures thereof.

10. The drug-eluting stent of claim 9, wherein the biodegradable polymer is chosen from tyrosine derived polycarbonates.

11. The drug-eluting stent of claim 9, wherein the biopolyesters are poly($\beta$-hydroxyalcanoate)s (PHAs) and derived compounds.

12. The drug-eluting stent of claim 1, wherein the drug-containing biodegradable polymeric layer has a thickness between 1 and 200 microns.

13. The drug-eluting stent of claim 1, further comprising a biodegradable topcoat layer.

14. The drug-eluting stent according to claim 13, wherein the biodegradable topcoat layer is made from the same composition as that of said drug-containing biodegradable polymeric layer.

15. The drug-eluting stent according to claim 1, wherein the drug comprised in said drug-containing biodegradable polymeric layer is an encapsulated drug.

16. The drug-eluting stent of claim 1, wherein the stent framework comprises a suitable biocompatible material.

17. The drug-eluting stent of claim 16, wherein the suitable biocompatible material comprises a material selected from the group consisting of stainless steel, nitinol, tantalum, cobalt-chromium MP35N, cobalt-chromium MP20N, platinum, titanium, and a combination thereof.

18. The drug-eluting stent of claim 16, wherein the suitable biocompatible material comprises an alloy.

* * * * *